Figure 1:
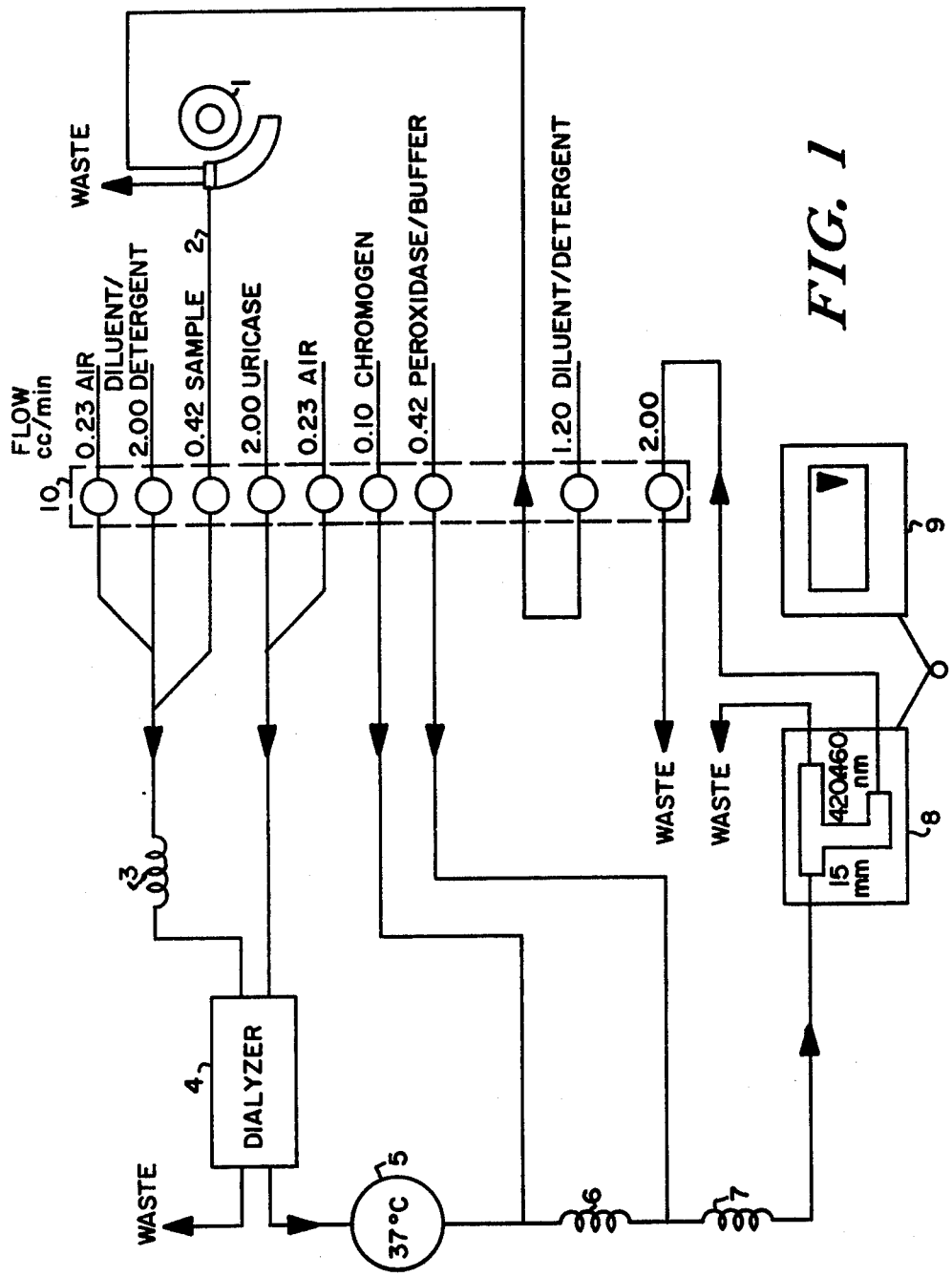

United States Patent [19]

Hunziker

[11] 4,095,948
[45] Jun. 20, 1978

[54] DETERMINATION OF URIC ACID

[75] Inventor: Paul Hunziker, Basel, Switzerland

[73] Assignee: Hoffmann-La Roche Inc., Nutley, N.J.

[21] Appl. No.: 707,596

[22] Filed: Jul. 22, 1976

Related U.S. Application Data

[63] Continuation of Ser. No. 513,794, Oct. 10, 1974, abandoned.

[30] Foreign Application Priority Data

Oct. 19, 1973 Switzerland ............... 14807/73

[51] Int. Cl.$^2$ .............. G01N 21/26; G01N 31/14; G01N 31/22; G01N 33/16
[52] U.S. Cl. ............. 23/230 B; 195/103.5 R; 252/408
[58] Field of Search .......... 23/230 B, 253 R; 252/408; 195/103.5 R

[56] References Cited

U.S. PATENT DOCUMENTS

| 3,335,069 | 8/1967 | Wachter | 23/230 B X |
| 3,489,525 | 1/1970 | Natelson | 23/253 R |
| 3,493,346 | 2/1970 | Hughes | 23/230 B |
| 3,554,701 | 1/1971 | Cottrell | 23/230 B |
| 3,649,198 | 3/1972 | Rush | 23/230 B |
| 3,653,841 | 4/1972 | Klein | 23/230 B X |
| 3,667,915 | 6/1972 | Klein | 23/230 B |
| 3,711,252 | 1/1973 | Roy | 23/230 B X |
| 3,733,177 | 5/1973 | Klein | 23/230 B |
| 3,801,466 | 3/1974 | Denney | 23/230 B X |
| 3,822,115 | 7/1974 | Morin | 23/230 B |

OTHER PUBLICATIONS

G. F. Domagk et al., Anal. Biochemistry, 22, 219-224 (1968).
D. Susic et al., Z. Anal. Chem., 257, 130-132 (1971).
Chemical Abstracts, 72:87090n (1970).
Chemical Abstracts, 71:27838g (1969).
Chemical Abstracts, 78:156196q (1973).

Primary Examiner—Sidney Marantz
Attorney, Agent, or Firm—Samuel L. Welt; Bernard S. Leon; R. Hain Swope

[57] ABSTRACT

An automated method for the determination of uric acid in biological fluids utilizing a benzidine or diphenyline and peroxidase as the color indicator.

28 Claims, 1 Drawing Figure

DETERMINATION OF URIC ACID

This is a continuation of application Ser. No. 513,794 filed Oct. 10, 1974, abandoned.

BACKGROUND OF THE INVENTION

There exists a need for an automated quantitative method for the determination of uric acid in biological liquids, e.g., urine, blood, blood serum or blood plasma, which is specific, requires only a small amount of test material, is sufficiently inexpesive to permit routine examinations, requires no special technical training and is well suited for clinical use. In addition, it is important that such an automated method works with sequential or continuous sample flow in order that a large number of samples can be processed rapidly and analyzed with great accuracy.

An automatic system is needed which works with a continuous or sequential sample flow and is capable of highly accurate results for the diagnostic testing of large numbers of people for the incidence of pathological amounts of uric acid in their blood. Uric acid is the end product of purine degradation in humans and is therefore found physiologically in blood. In numerous diseases, there is an increase or decrease in the uric acid concentration and therefore the determination of a variation from the normal physiological uric acid level in blood is an extremely important diagnostic indication for the physician.

Increases in the uric acid concentration are found, for example, in gout, chronic pneumonia with extensive destruction of tissue and pernicious leukemia. Decreases in uric acid concentration are found, for example, in the toxic lesions of the renal tubuli in Wilson's disease.

It is therefore important to have available an automated method for the determination of uric acid which is not only simple to carry out but which is also accurate and which can serve as an adjunct to routine screening examinations in clinics or to periodic screening examinations of cases in hospitals or nursing homes and the like.

The known methods for the determination of uric acid can be broadly classified as enzymatic, alkaline phosphotungstate and miscellaneous chemical colorimetric methods. The enzymatic method utilizing the enzyme uricase suffers the disadvantage that the measurement is carried out in the ultraviolet region. Such methods require the use of expensive quartz cuvettes and a spectrophotometer. In the alkaline phosphotungstate method the measurement is carried out in the visible region, but this method has the disadvantage that other components which act in a reductive manner are detected at the same time, thus producing values which are too high and, at the same time, incorrect.

An especially interesting method for the enzymatic determination of uric acid has been described recently by G. F. Domagk and H. H. Schlicke in Analytical Biochemistry 22, 219–224 (1968). The Domagk et al. method combines the advantage of specific enzymatic determination with the advantage of the ability to carry out the measurement in the visible region. According to this method, uric acid is converted in a first step using uricase into allantoin and hydrogen peroxide.

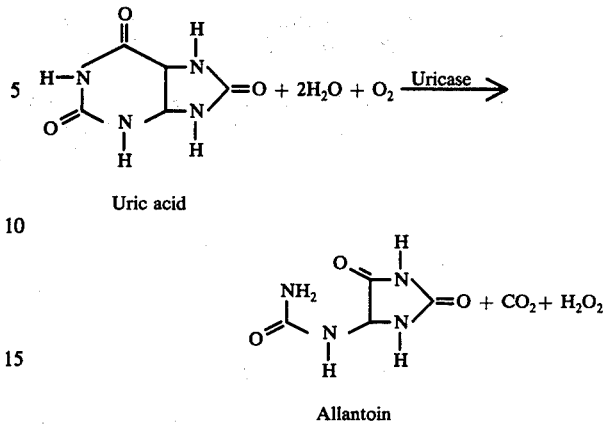

Uric acid

Allantoin

In the second step a color forming indicator reagent (chromogen) is introduced. The hydrogen peroxide resulting from the first step oxidizes the chromogen which is present in the leuco-form to a colored substance, under the catalytic action of peroxidase. o-Dianisidine is such a chromogen.

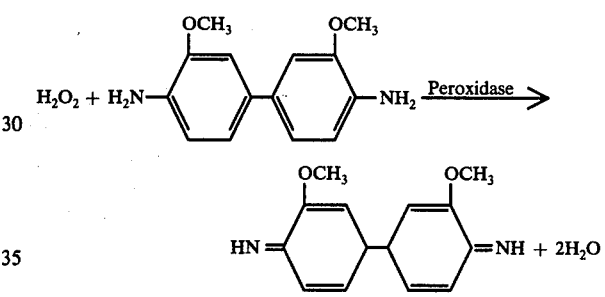

One of the disadvantages of this method is, however, the time-consuming deproteinization step required before the determination is actually carried out. This deproteinization method is described for a manual procedure and is not suitable for automation according to the procedures of D. Susic and P. Scheibe, Z. Anal. Chem. 257, 130-132 (1971).

DESCRIPTION OF THE INVENTION

The present invention provides a sensitive, highly accurate, simple automated method for determining uric acid which has a large linear range and slight susceptibility to adverse side reactions from both chemical and technical respects.

More particularly, the present invention is concerned with a method for the quantitative determination of uric acid in biological fluids, e.g., urine, blood, blood serum or blood plasma, which process comprises carrying out the following steps sequentially in continuous flow;

(a) combining, in continuous flow, a measured sample of a specimen of test fluid with an aqueous dilution solution, (b) passing the resulting mixture through a dialysis zone, thereby separating from said mixture a clear aqueous solution, (c) mixing said clear aqueous solution with a buffered uricase solution having a pH between 8.5 and 10, (d) incubating the resulting aqueous solution, (e) mixing at pH 5.5 to 8.5 the hydrogen peroxide obtained according to step (d), by sequential or concurrent flow, with a first reagent comprising a chromogen in the leuco-form, e.g., an unsubstituted or nuclear-substituted benzidine or diphenyline, and a second reagent comprising peroxidase to produce a colored solution and (f) flowing the colored solution to an analyzing zone, e.g., through a flow cuvette, and photometrically determining the uric acid content present in the sample during the flow of the colored solution through the analyzing zone.

In step (a) suitable aqueous diluents are aqueous solutions of alkali or alkaline earth metal salts such as, for example, sodium chloride, sodium tetraborate, potassium chloride or calcium chloride, with sodium chloride being preferred. The concentration of alkali or alkaline earth metal salt depends on the specific salt being used. In the case of the preferred salt, sodium chloride, a concentration between about 1.2 and 2.0% by weight is preferred, with a concentration of about 1.3% being especially preferred.

In step (b) the mixture from step (a) is passed through a dialyzer for the purpose of deproteinization to obtain a clear aqueous solution separated from the mixture. The type of dialyzer is not critical. It is preferred, however, to use a dialyzer with a dialyzation path of 30 to 100 cm. The dialysis takes about 5 to 40 seconds.

In step (c), the clear aqueous deproteinized solution is combined with a buffered uricase solution in the dialyzer. Preparations isolated from animal organs are used as the uricase, e.g., pigs' liver uricase. The uricase is dissolved in an aqueous buffer having a pH of from 8.5 to 10 prior to combining it with the deproteinized solution. Generally, any conventional buffer mixture which is suitable for maintaining such a pH range can be used. However, a borate buffer is preferably used, especially a sodium tetraborate buffer. The concentration of the buffer in the buffer/uricase solution depends on the buffer being used. In the case of sodium tetraborate, the concentration expediently lies between 5 and 15 mmol/liter. A concentration of 10 mmol/liter is preferred. The activity of the uricase needed in the solution depends on the buffer being used. In the case of sodium tetraborate, this activity amounts to at least 2 units per liter. 10 Units per liter is preferred. Thus in the case where sodium tetraborate is the buffer, from about 2 to 10 units of activity of uricase is needed. A unit of uricase activity is defined as follows:

One unit or uricase activity corresponds to the conversion of 1 micromole of uric acid per minute and per liter, determined at a temperature of 25° C.

In order to complete the conversion of uric acid into allantoin and hydrogen peroxide, the aqueous solution is incubated. The temperature at which the incubation is carried out is not critical, but it advantageously lies at about 37° C. The duration of the incubation depends on several parameters such as, for example, the temperature, the dialysis path and the uricase activity. Four minutes is a preferred incubation time.

After the incubation, the resulting hydrogen peroxide is reacted, in step (e), with a chromogen in the leuco-form under the catalytic action of peroxidase. Typical suitable chromogens are nuclear-substituted or unsubstituted benzidine (4,4'-diaminobiphenyl) or diphenyline (2,4'-diaminobiphenyl). Suitable nuclear-substituted benzidines are, for example, o-dianisidine and o-tolidine. These chromogens are added in aqueous solution. The concentration of the chromogen is not critical and, in the case of o-dianisidine, is advantageously 1.3 mg./ml. The peroxidase is added in the form of an aqueous solution which is preferably buffered. A preferred peroxidase is that isolated from horseradish.

The activity of the peroxidase in the solution depends on the buffer which is used, but advantageously amounts to at least 0.04 units/ml., with 0.4 units/ml. being preferred. Thus, the activity of the peroxidase is preferably between 0.04 and 0.4 units/ml. A unit of peroxidase activity is defined as follows:

One unit of peroxidase activity corresponds to the conversion of 1 micromole hydrogen peroxide per minute and per liter, determined at a temperature of 25° C.

The peroxidase solution is preferably buffered to a pH between about 5.5 and 8.5. Any conventional buffer mixture which is suitable for maintaining such a pH range can be used. A phosphate buffer of pH 7.5 is preferably used. The sequence of addition of the leuco-coloring substance (chromogen), the buffer and the peroxidase is not important, but it is preferable to first add the solution of the leuco-coloring substance and subsequently the buffered peroxidase solution.

Finally, in step (f), the extinction of the colored solution obtained is measured in a photometer. In the case of o-dianisidine, this measurement is carried out at between 420 and 460 nm. The results of the photometric measurement are recorded by means of a suitable recording apparatus.

One embodiment of the automated method in accordance with the invention is illustrated in FIG. 1 appended hereto.

FIG. 1 illustrates an automatic system having a continuous flow, wherein the sample to be analyzed is sucked successively out of separate sample containers by the sample tube 2 (flow 0.42 cc/minute). The sample plate 1 rotates at constant speed and provides the system with 60 samples per hour with a washing ratio of 5:1. This washing is effected by means of a diluent/detergent mixture containing preferably 0,25% (vol./vol.) of detergent flowing through the sample tube 2 (flow 120 cc/minute). A sample sucked out in this manner is mixed in flow with a 1.3% sodium chloride solution (flow 2.00 cc/minute) and led through a conventional mixing spiral 3 having 5 glass windings. After the mixture has passed through the mixing spiral, it is pumped through a dialyzer 4 (dialysis path 60 cm) which is provided with a Cellophane membrane or the like, the uric acid passing by dialysis into the buffered uricase solution (pH = 9.5) delivered into the lower part of the dialyzer (flow 2.00 cc/minute). After passage through the dialyzer, the mixture is incubated at a temperature of 37° C. for 4 minutes in a heating bath 5, the uric acid being quantitatively reacted to give allantoin and hydrogen peroxide. An aqueous solution of o-dianisidine is then continuously added to the resulting mixture (flow 0.10 cc/minute). Subsequently, this mixture is led through a mixing spiral 6 having 20 glass windings. After flowing through the mixing spiral 6, a buffered aqueous peroxidase solution of pH 7.0 is added (flow 0.42 cc/minute), the resulting mixture having a pH of 7.5. The mixture is then led through a second mixing spiral 7 having 20 windings. In flowing through the mixing spiral 7, the hydrogen peroxide reacts with the o-dianisidine under the catalytic action of the peroxidase to form a yellow-orange coloration. Subsequently, photometric measurements are carried out at 460 nm in a photometer 8 in a 15 mm flow cuvette, i.e., the extinction of the solution tested is measured at 460 nm in a photometer with a flow cuvette. The results of thephotometric measurement are recorded using a suitable recording apparatus 9.

The continuous flow system illustrated in FIG. 1 sucks out 60 samples/hour. The materials which flow into the system are pumped in by means of a suitable proportioning pump 10 which is adjusted to maintain the desired flow velocities. In order to avoid contamination, the dilution solution and the buffered uricase solution are separated by air bubbles (flow 0.23 cc/minute). In order to produce a regular bubble pattern, a detergent is added to both of these solutions and to the buffered peroxidase solution. A suitable detergent is, for example, polyoxyethylene sorbitan monolaurate (Tween 20). The concentration of the added detergent preferably amounts to 0.25% for the dilution solution and preferably to 1% for the other two solutions.

In a further aspect of the present invention, the preparations required for the method in accordance with the present invention are packed in a diagnostic reagent kit or in a diagnostic reagent system. In such a reagent system, the reagents are packed in amounts which allow the preparation of stock solutions which are suitable for routine examinations. The amount of reagent which is required in a specific reagent system can be readily calculated in relation to the sample to be examined with the aid of the aforementioned molar amounts respective of enzyme activity. These calculations will be familiar to the person skilled in the art.

| Reagent A | 10 units of uricase (suspension) |
|---|---|
| Reagent B | 60 mmol of phosphate buffer (granulate) 100 units of peroxidase (lyophilisate) |
| Reagent C | 66 mg. of o-dianisidine (lyophilisate) |
| Reagent D | 18 ml. of Tween 20 (viscous liquid) |
| Reagent E | 10 mmol of sodium tetraborate (crystalline powder) |

The reagent system can be used for the performance of about 500 determinations. The volume of sample required for each determination is about 0.4 m. These reagents are stable for at least 1 year at 2°–8° C.

The following Examples illustrate the present invention.

EXAMPLE 1

A series of dilutions of aqueous uric acid standards were prepared with the following concentrations: 2 mg./100 ml., 5 mg./100 ml., 100 mg./100 ml., 20 mg./100 ml., 30 mg./100 ml. and 40 mg./100 ml. These standards were used as samples and determined in the specific embodiment of the method in accordance with the invention illustrated by FIG. 1.

Table I

| Uric Acid Concentrations (mg./ml.) | Result in Scale Divisions |
|---|---|
| 2 | 4.4 |
| 5 | 11.1 |
| 10 | 22.3 |
| 20 | 44.4 |
| 30 | 65.0 |
| 40 | 87.3 |

Table I shows that a reliable linear range up to 40 mg./ml. is guaranteed by the method in accordance with the invention.

EXAMPLE 2

The uric acid content of five different control sera was determined using the specific embodiment of the method in accordance with the invention illustrated by FIG. 1. The result is given in Table II.

Table II

| Serum | $\bar{x}$ | s | VC | N |
|---|---|---|---|---|
| a | 4.50 | 0.054 | 1.20 | 15 |
| b | 4.17 | 0.049 | 1.18 | 15 |
| c | 9.11 | 0.012 | 0.13 | 10 |
| d | 4.39 | 0.032 | 0.73 | 10 |
| e | 4.88 | 0.07 | 1.43 | 10 |

$\bar{x}$ = Average value mg. uric acid/100 ml.
s = Standard deviation
VC = Variation coefficient (%)
N = Number of determinations carried out in the series.

Table II shows an average variation coefficient of less than 1% and therefore shows the precision of the method.

EXAMPLE 3

To 2 different control sera were added respectively 0.93 mg./100 ml., 1.86 mg./100 ml. and 2.79 mg./100 ml. of uric acid and the uric acid content was determined using the specific embodiment of the method in accordance with the invention illustrated by FIG. 1.

The results illustrating the recovery of uric acid are given in Table III.

Table III

| Uric acid in sample mg/100 ml | Uric acid added mg/100 ml | Total amount of uric acid mg/100 ml | Recovered uric acid mg/100 ml | Recovery % |
|---|---|---|---|---|
| 4.50 | 0.93 | 5.43 | 5.39 | 99.3 |
| 4.50 | 1.86 | 6.36 | 6.35 | 99.8 |
| 4.50 | 2.79 | 7.29 | 7.30 | 100.2 |
| 8.96 | 0.93 | 9.89 | 10.08 | 102 |
| 8.96 | 1.86 | 10.82 | 10.99 | 101.5 |
| 8.96 | 2.79 | 11.75 | 11.68 | 99.4 |
| | | | Average: | 100.36 |

EXAMPLE 4

To a control serum having an original uric acid content of 4.6 mg./100 ml. were added respectively 10 mg./100 ml. of glutathione, 10 mg./100 ml. of allantoin and 5 mg./100 ml. of creatinine and then the uric acid content was determined using the embodiment of the method in accordance with the invention illustrated by FIG. 1.

The results are given in Table IV.

Table IV

| Sample | Foreign substance added | Theoretical value mg/100 ml | Value found mg/100 ml |
|---|---|---|---|
| 1 | — | 4.6 | 4.6 |
| 2 | Glutathione, 10 mg/100 ml. | 4.6 | 4.6 |
| 3 | Allantoin, 10 mg/100 ml. | 4.6 | 4.7 |
| 4 | Creatinine, 5 mg/100 ml. | 4.6 | 4.7 |

Table IV illustrates the slight susceptibility to adverse side reactions of the method of this invention with respect to glutathione, allantoin and creatinine.

EXAMPLE 5

A standard having a concentration of 30 mg. of uric acid per 100 ml. was prepared. An aliquot part of this standard was treated with ascorbic acid such that the total concentration of ascorbic acid amounted to 5 mg./100 ml. Subsequently, the two standards were used as samples in the system and the content of uric acid was measured using the embodiment of the method illustrated by FIG 1.

| Result: | |
|---|---|
| Sample without ascorbic acid | 30.0 mg. of uric acid/100 ml. |
| Sample with ascorbic acid | 30.2 mg. of uric acid/100 ml. |

The foregoing result shows the slight susceptibility to adverse side reactions of the method of this invention with respect to ascorbic acid.

I claim:

1. A method for the quantitative analysis of uric acid in biological fluids consisting essentially of providing in continuous flow the sequential steps comprising:
   (a) combining, in continuous flow, a measured sample of a specimen of test fluid with an aqueous solution of an alkali metal or alkaline earth metal salt diluent;
   (b) passing the resulting mixture through a dialysis zone, thereby separating from said mixture a clear aqueous solution;
   (c) mixing said clear aqueous solution with a buffered uricase solution with a pH of 8.5 to 10;
   (d) incubating the resulting aqueous solution;
   (e) mixing at pH 5.5 to 8.5 the hydrogen peroxide produced in step (d), by sequential or concurrent flow, with a first reagent comprising a buffered aqueous solution of a chromogen in the leuco form consisting of an unsubstituted or nuclear-substituted benzidine or diphenyline and a second reagent comprising a buffered aqueous solution of peroxidase, thereby forming a colored solution; and
   (f) flowing said colored solution to an analyzing zone and photometrically determining quantitatively, during the flow of said colored solution through said analyzing zone, the uric acid content of the sample.

2. A method according to claim 1, wherein said diluent is an aqueous sodium chloride solution having a weight concentration of 1.1 to 1.4% sodium chloride.

3. A method according to claim 2, whereing said diluent contains 1.3% by weight sodium chloride.

4. A method according to claim 1 wherein the diluent contains a detergent.

5. A method according to claim 2 wherein the diluent contains a detergent.

6. A method according to claim 4, wherein said detergent is polyoxyethylene sorbitan monolaurate.

7. A method according to claim 5 wherein said detergent is polyoxyethylene sorbitan monolaurate.

8. A method according to claim 1 wherein the buffer used in step (c) is a borate buffer.

9. A method according to claim 8 wherein the buffer is sodium tetraborate.

10. A method according to claim 8, wherein the pH is 9.5.

11. A method according to claim 1 wherein the activity of the uricase is at least 2 units per liter.

12. A method according to claim 11, wherein the activity of the uricase is about 10 units per liter.

13. A method according to claim 1 wherein in step (c) a detergent is added.

14. A method according to claim 13, wherein the detergent is polyoxyethylene sorbitan monolaurate.

15. A method according to claim 14, wherein the concentration of polyoxyethylene sorbitan monolaurate is about 1%.

16. A method according to claim 1 wherein the incubation of step (d) is carried out at a temperature of about 37° C.

17. A method according to claim 16 wherein the incubation is carried out for about 4 minutes.

18. A method according to claim 1, step (e), wherein the chromogen is a nuclear-substituted benzidine.

19. A method according to claim 18, wherein the nuclear-substituted benzidine is o-dianisidine.

20. A method according to claim 19, wherein the concentration of o-dianisidine is about 1.3 mg./ml.

21. A method according to claim 1, step (e), wherein there are 0.4 units per ml. of peroxidase.

22. A method according to claim 1, step (e), wherein the buffer is a mixture of phosphate buffer.

23. A method according to claim 22, wherein the buffer is a mixture of primary and secondary sodium phosphate.

24. A method according to claim 1, step (e), wherein the pH is about 7.0

25. A method according to claim 1 wherein in step (e) the flow is sequential.

26. A method according to claim 25, wherein the detergent is simultaneously added with the peroxidase.

27. A method according to claim 1, step (f), wherein the photometric determination is carried out between 420 and 460 nm.

28. A method according to claim 1 wherein the test fluid is blood plasma or blood serum.

* * * * *